United States Patent [19]

Nallakrishnan

[11] Patent Number: 5,552,822
[45] Date of Patent: Sep. 3, 1996

[54] APPARATUS AND METHOD FOR SETTING DEPTH OF CUT OF MICROMETER SURGICAL KNIFE

[76] Inventor: Ravi Nallakrishnan, 26 Plaza Dr., Westmont, Ill. 60559

[21] Appl. No.: 150,851

[22] Filed: Nov. 12, 1993

[51] Int. Cl.⁶ ................................................. H04N 7/18
[52] U.S. Cl. ........................... 348/79; 73/104; 348/141
[58] Field of Search ................. 348/79, 141; 73/104; H04N 7/18

[56] References Cited

U.S. PATENT DOCUMENTS

| | | | |
|---|---|---|---|
| 3,606,550 | 9/1971 | Proska | 73/104 |
| 3,908,077 | 9/1975 | Stut | 348/141 |
| 4,207,594 | 6/1980 | Morris | 348/141 |
| 4,662,075 | 5/1987 | Mastel | 33/628 |
| 4,691,715 | 9/1987 | Tanne | 128/774 |
| 4,744,362 | 5/1988 | Gründler | 128/305 |
| 4,750,489 | 6/1988 | Berkman | 128/314 |
| 4,781,463 | 11/1988 | Rosen | 348/141 |
| 4,922,909 | 5/1990 | Little | 128/630 |
| 5,098,426 | 3/1992 | Sklar | 606/5 |
| 5,131,753 | 7/1992 | Pine | 73/404 |

*Primary Examiner*—Howard W. Britton
*Attorney, Agent, or Firm*—Jerry A. Schulman

[57] ABSTRACT

Apparatus and methods for determining or verifying the depth of cut of a micrometer surgical knife include placing the knife within the viewing field of a video microscope to produce an image on a video monitor, generating cursor lines on the monitor, spacing the cursor lines apart by a distance which, when calibrated to the actual dimensions of the knife, represents the actual, linear cutting depth, zeroing the knife by moving it until the footplate of the knife is aligned with one cursor line and moving the knife blade to extend past the footplate to the second cursor line. Alternatively, the footplate is aligned with the first cursor line and the second cursor line is aligned with the blade tip, and the resulting distance between the first and second cursor lines is correlated to an actual, linear dimension.

8 Claims, 3 Drawing Sheets

APPARATUS AND METHOD FOR SETTING DEPTH OF CUT OF MICROMETER SURGICAL KNIFE

The present invention relates generally to surgical knives and, in particular, apparatus and methods to set the depth of cut of a surgical knife having a micrometer mechanism to set the blade exposure.

BACKGROUND OF THE INVENTION

A particular form of ophthalmic surgery known as radial keratotomy requires making incisions in the cornea of the eye. These incisions must be made accurately and to no more than a selected depth. Surgical knives designed for this purpose often include a type of micrometer drive or mechanism to enable the surgeon to extend the cutting surface of the blade beyond a footplate or guide formed on the knife by a distance equal to the selected depth of the cut.

Due to the delicate nature of ophthalmic surgery, it is desirable to provide highly accurate depths of cut and to provide backups or double checks of the depth of cut. This is particularly so when the depth of cut may be set prior to surgery. When the depth of cut must be changed during surgery, it is advantageous to provide a means for making the change quickly, conveniently and in a manner which allows the depth of cut to be verified. It is also an advantage to have a system for verifying or setting depth of cut that makes it easier to maintain the sterility of the instruments being used.

Prior efforts of others to provide a means for setting the depth of cut of such knives include apparatus such as block gauges or coin gauges, wherein the knife is positioned against a gauge and the blade is then extended until it physically contacts the gauge. Examples of such prior art gauges are found in U.S. Pat. No. 4,662,075 (Mastel, et al.), at FIGS. 1A and 1B.

Use of mechanical gauges with micrometer knives has certain inherent disadvantages. The blades on such knives (typically formed from diamond or sapphire) must be extremely sharp to avoid tearing the tissue of the eye during surgery. This means using a diamond or sapphire knife blade which, while extremely sharp, are also susceptible to damage if the tip of the blade is abutted against a hard surface such as that of the gauge. Mastel, et al. also point out that the use of such gauges also creates the risk of parallax errors in reading the gauge scales, and that error also results over time as the gauges suffer material degradation or wear.

Instead of such mechanical depth-setting gauges, Mastel, et al. teach and describe a microscope with a stage having a holder for the knife and a field of magnification within which the tip of the knife blade is positioned and viewed. According to the teachings of Mastel, et al., the microscope's field of view has a reticle axis which appears to the user as a vertically-extending line. This axis is used as a line of reference for setting the depth of cut.

The knife to be set is clamped into a holder mounted to a tray which, in turn, is mounted to the stage of the microscope in such a manner as to allow the tray to be moved in relation to the stage by a screw-and-spindle mechanism operable through use of a micrometer dial in a direction perpendicular to that of the reticle.

The knife preferably includes a micrometer handle, the operation of which allows the knife blade to be extended from or withdrawn into the handle. When placed in the holder, the knife's footplate or guide faces the reticle, and the knife blade is fully retracted. The micrometer handle is then used to operate the spindle and advance the knife toward the reticle until the footplate or guide is aligned with the reticle. At this point, the micrometer which controls the motion of the tray is "zeroed" that is set to a zero scale reading and is then rotated to move the tray away from the reticle by a distance equal to that of the depth of the cut. Next, the micrometer handle of the knife is rotated to advance the knife blade while the user observes the reticle through the microscope eyepiece. When the blade tip just reaches the reticle, it is extended beyond the footplate or guide by a distance equal to the depth of the cut and is then removed from the holder to be used in surgery. In this manner, the depth of cut may be set without physical contact between the blade and a mechanical guide and without the concomitant risk of damage to the blade tip.

Use of the Mastel, et al. device calls for a number of physical operations. The knife to be used is first secured to a tray mounted on a moveable stage which, in turn, is mounted to a base. The stage can be moved in both the x- and y-axis direction with respect to the base. A micrometer spindle is used to move the stage in the x-axis direction.

A microscope is mounted to the same base and is positioned to allow the movement of the table to bring the knife blade into the microscope's field of vision. Typically, the knife is of the type having a micrometer mechanism used to adjust movement of the knife blade into or out of the knife handle, and a footplate beyond which the blade must be extended for cutting. Once the knife blade is within the microscope's viewing field, the table is moved to align the knife's footplate with a reticle formed on the microscope lens. This requires that the surgeon concentrate on focusing the microscope on the footplate and, thereafter, manipulating the micrometer to advance the knife blade to align the blade tip with the reticle as well. The surgeon then "zeroes" the micrometer spindle on the moveable stage and then uses the spindle to move the stage along an axis perpendicular to the reticle for a distance equal to the selected depth of cut. Thereafter, the surgeon uses the knife's micrometer mechanism to advance the blade until the blade tip again aligns with the reticle. With the cutting depth now set, the knife is removed from the tray and is ready to use. A brief description of the Mastel, et al. device is found in the '075 patent at Column 3, lines 3–41.

Use of the foregoing method and apparatus requires the surgeon to peer into the microscope during initial setting and any eventual verification of the depth of cut setting, at a time when the surgeon is gowned, masked and gloved, and is striving to keep a sterile operating field. The surgeon risks contamination of the gloves he or she is wearing every time a micrometer spindle is manually touched and adjusted. Mastel, et al. do make provisions for using sterilized sleeves to cover the microscope's operating controls, but this creates yet another potential source of contamination and another set of details to consider at a time when the surgeon is already preoccupied with the details and procedures of surgery.

Even if the knife, or knives, are adjusted prior to surgery, the surgeon may well wish to verify the depth of cut immediately prior to making an actual incision. While Mastel, et al., describe several ways to verify the setting obtained with the microscope, they involve prior art procedures such as viewing the micrometer setting on the knife or using a "certified" gauge block mounted to the table.

U.S. Pat. No. 4,750,489 (Berkman, et al.), teaches and describes a radial keratotomy (RK) knife of the general type described above and which has a linear variable differential transformer incorporated as part of the knife structure. The knife is inserted into an electrical console which is used to set the depth of cut by measuring the position of the transformer within the knife. A method for zeroing the blade utilizes a membrane inside the console is contacted by the knife's footplate and a laser to project a beam focused at the footplate. An optical detector detects changes in the beam's characteristics which occur when the knife blade is advanced to contact the membrane and thus signals the "zero" point of the knife.

U.S. Pat. No. 4,744,362 (Grundler) teaches and describes a device for performing keratoplasty automatically rather than by hand and which features a monitor used by the machine operator to observe the various steps of the operation as the machine carries them out.

U.S. Pat. No. 4,922,909 (Little, et al.) teaches and describes a video monitoring system for use in surgery where a computer is used to store tissue images which can then be retrieved and compared to the appearance of the tissue at later stages of treatment or surgery.

U.S. Pat. No. 4,691,715 (Tanne) teaches and describes an automatic corneal surgery system using a series of probes to map the surface of the cornea. A computer then processes the information and uses it, along with information as to the electrical resistivity of the cornea, to control the movement and depth of cut of a cutting blade. Depth of cut is set by the vertical movement of the blade.

U.S. Pat. No. 5,098,426 teaches and describes a method and apparatus for precision laser ocular surgery utilizing a surgical video microscope which projects an image to a video monitor. A series of ruling lines projected onto the tissue surface provides further information as to tissue dimensions, contours, etc. sufficient to guide a laser beam used as part of surgery.

There are also known high resolution video measuring systems such as the VIA®-100 Video Measurement System sold by Boeckler Instruments, Inc. of Tucson, Ariz., and the Imagen HR 1024™ sold by Optech Instrument Corporation of Greenvale, N.Y. Both are "edge-finding" optical systems using a video microscope to produce a high-resolution video image fed to a processing unit which, when calibrated, can accurately measure the object being scanned.

Against this background of prior art, there exists the need for a calibration system useful to set the cutting depth on micrometer-adjustable surgical knives to be used manually during surgery.

The need also exists for such a system which can be conveniently used by a surgeon during surgical procedures to set, reset or verify the cutting depth of a particular knife without unnecessarily interrupting surgery or risking violation of the sterile field.

The need further exists for such a system to be adaptable for use with a wide variety of surgical knives.

The need also exists for such a system to zero and set the cutting depth on surgical knives without physical contact between the system and the knife tip.

The need also exists for such a system to allow for verification or change of the cutting depth while minimizing the efforts needed to maintain sterility of the instrument and the system components.

BRIEF DESCRIPTION OF THE INVENTION

A microscope is fitted with a video head and a stage to which a clamp is attached. The clamp is adapted to hold a surgical knife generally of the type having a footplate which acts as a datum surface or "zero-point" in determining depth of cut and a micrometer mechanism used to advance a surgical cutting blade past the footplate or datum. The video head broadcasts an image of the footplate and blade to a television monitor. Calibration apparatus is provided to scribe a first linear cursor on the video screen and position the cursor to coincide with the plane of the footplate and to scribe on the screen a second linear cursor parallel to the first linear cursor. The calibration apparatus allows the scaled movement of the second cursor in relation to the first cursor to create an on-screen offset equal to the desired depth of cut. The micrometer mechanism of the knife is then operated to move the blade until the on-screen blade image reaches the second cursor, thus setting the depth of cut. Such an apparatus eliminates the necessity for a surgeon to manually adjust a microscope while peering in a relatively small field of view to adjust cutting depth, and also eliminates the need for complex and costly laser apparatus.

BRIEF DESCRIPTION OF THE DRAWINGS

These and other features and characteristics of the present invention will be more apparent upon consideration of the following drawing figures, in which.

DETAILED DESCRIPTION OF THE INVENTION

Figure 1:
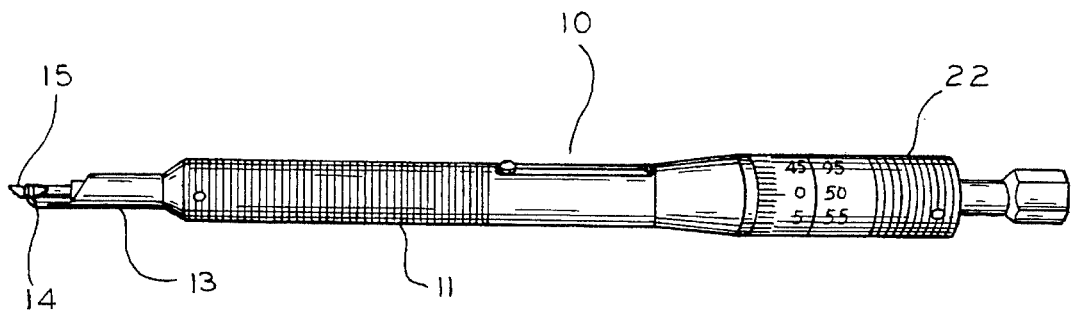
FIG. 1 is an elevational view of a surgical knife of the type used in ophthalmic surgery.

Referring now to FIG. 1, the numeral 10 indicates generally a surgical knife of the type commonly used in ophthalmic surgery. Knife 10 has a hollow handle 11, at one end of which a micrometer mechanism 12 is mounted and, at the other end of which a hollow sheath 13 is attached. At the terminus of sheath 13 is a footplate 14. A bladeholder mounted within handle 11 moves axially as micrometer 12 is rotated with respect to handle 11 to selectively extend or retract a surgical cutting blade 15. Blade 15 must be extended beyond footplate 14 to expose a sharpened edge used to cut ophthalmic tissue. During the surgical procedure known as radial keratotomy, footplate 14 rests upon the cornea as knife blade 15 is used to make incisions in the cornea. The incision depth is determined by the distance blade 15 is advanced from handle 11 beyond footplate 14. This distance can be set by using micrometer 12 to measure the distance blade 15 moves past footplate 14. The present invention provides other means to set or verify the depth of cut, or to facilitate a change in the depth of cut during surgery.

Figure 2:
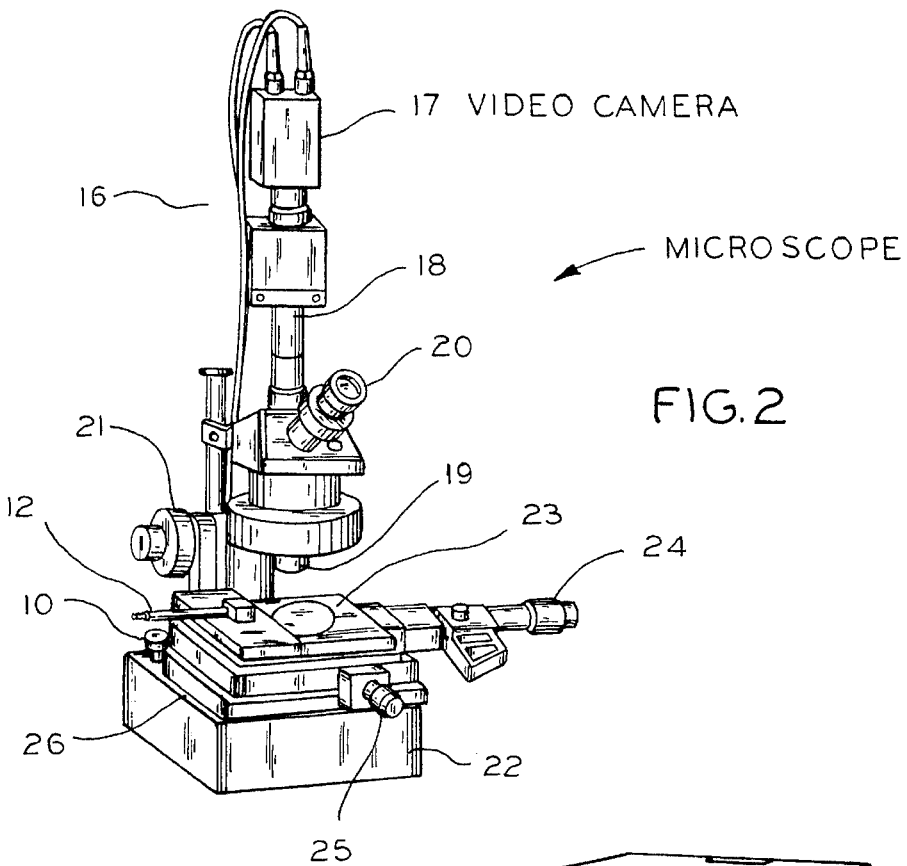
FIG. 2 is a perspective view of a video microscope of the type used in the present invention.

Referring now to FIG. 2, the numeral 16 indicates generally a microscope equipped with a video camera 17 mounted to a body tube 18 providing a video output of the field of vision of objective lens 19. A conventional eye piece 20 allows visual inspection, and focus knob 21 is used to focus objective lens 19 for either the video or manual uses of microscope 16.

Microscope 16 is mounted to a base 22 which also supports a compound stage 23, of the general type described in the Mastel, et al. reference (U.S. Pat. No. 4,662,075) having platforms moveable at right angles to each other in both fore-and-aft (x-axis) and side-to-side (y-axis) directions. Movement of one such platform along the x-axis is controlled by x-axis micrometer 24, while movement of the other platform along the y-axis movement is controlled by y-axis micrometer spindle 25. Stage clamp 26, described more fully hereinbelow, is used to clamp knife 10 during zeroing, setting and verifying operations, and moves as the above-described stage platforms are moved. In another variation, clamp 26 may actually comprise one of the moveable platforms.

Figure 3:
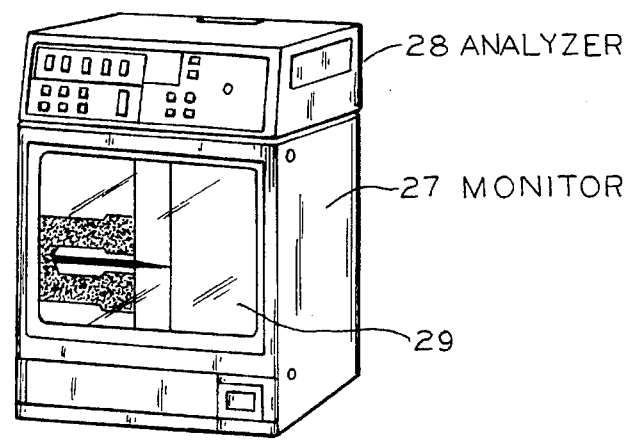
FIG. 3 is a perspective view of a video monitor and controller of the type used in the present invention.

In FIG. 3 is shown a video monitor 27 and a control console 28, used to process the video signal received from video camera 17 and transmit it, along with other information, to screen 29 of monitor 27. One control console used successfully with the present invention is the VIA®-100, sold by Boeckler Instruments, Inc.: another, sold by Optech Instrument Corporation, is part of its Imagen™ HR 1024 series high resolution video measuring system. Console 28 not only transmits an image of the object placed within the viewing field of microscope 16, it also generates lines, or cursors that are superimposed on the screen of monitor 27 to be used as reference lines in a manner to be described hereinbelow.

Figure 4:
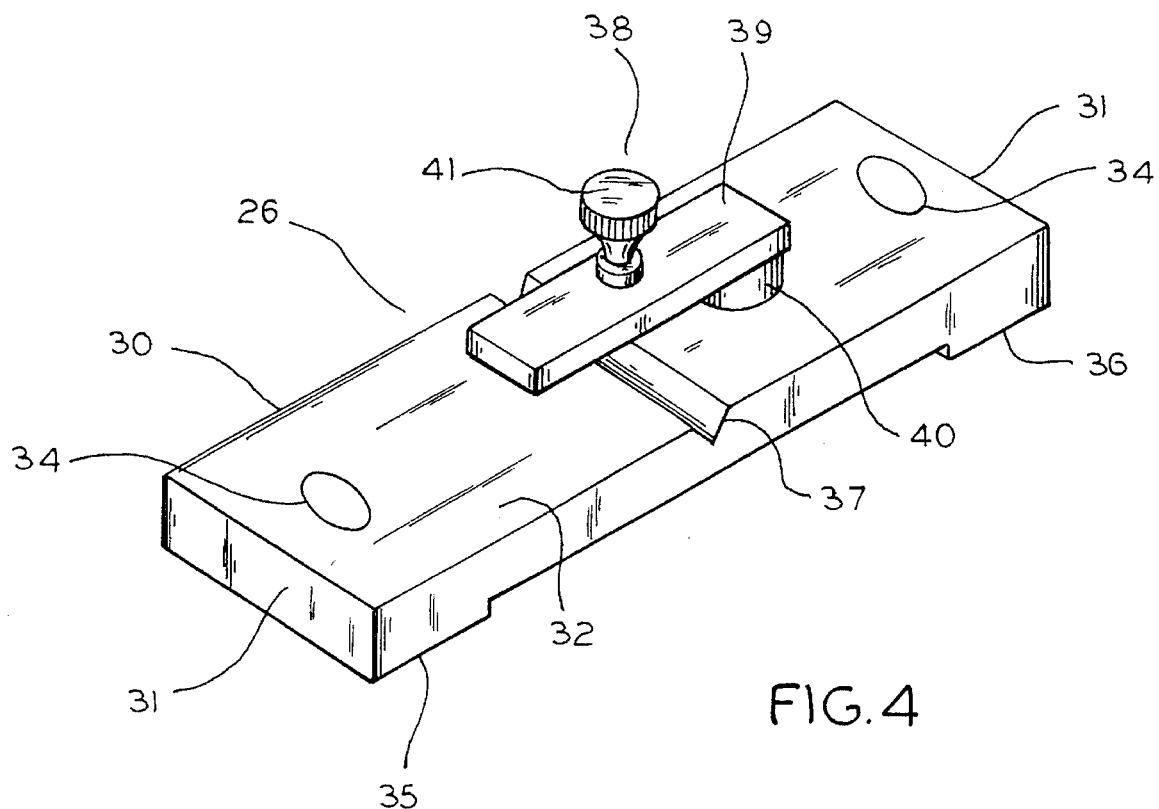
FIG. 4 is a top view of the clamp used to secure the knife of FIG. 1 to the microscope stage of FIG. 2.
Figure 5:
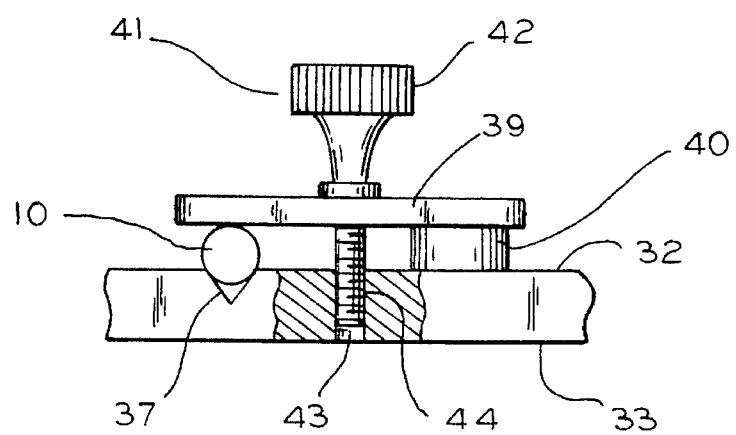
FIG. 5 is a side view of the clamp used to secure the knife of FIG. 1 to the microscope stage of FIG. 2.

Referring now to FIGS. 4 and 5, a stage clamp 26 is shown, a preferred embodiment of which has a solid, generally rectangular body 30 with end surfaces 31, an upper surface 32 and a bottom surface 33. A pair of mounting apertures 34 are formed on clamp body 31, extending all the way through from upper surface 32 to lower surface 33. As seen in FIG. 2, stage clamp 26 is attached to microscope stage 23: the preferred manner of attachment is by threaded fasteners passing through apertures 34 and threaded into tapped apertures formed on stage 23 (not herein specifically shown). In the example shown, a pair of offsets 35 and 36 are formed at bottom surface 33 as a part of body 30 to provide clearance for other components that may be present on stage 23 and over which stage 26 must be positioned during use.

A clamp groove 37, seen in FIGS. 4 and 5, is formed as part of upper surface 32 and, in this embodiment, is placed intermediate apertures 34 and parallel to end surfaces 31.

Located proximate to groove 37 and extending thereover is a clamp assembly 38, consisting of a clamp arm 39, a fulcrum 40 and a thumbscrew 41, having a knurled head 42 and a threaded shaft 43. Shaft 43 is threaded into a tapped aperture 44 formed as a part of clamp body 30 as seen in FIG. 5. In use, clamp arm 39 is deflected toward upper surface 32 as thumbscrew 41 is rotated to thread shaft 43 into aperture 44. In this fashion, an object placed in groove 37 (such as knife 10) will be quickly and firmly clamped into groove 37 as arm 39, deflected by thumbscrew 41, contacts knife 10 and presses it into groove 37.

Preferably, clamp 26 and all components attached thereto, including all securing screws and fasteners, are made from a material which is durable and easily sterilized, such as stainless steel and clamp 26 may be sterilized prior to mounting it to microscope stage 23.

Figure 6:
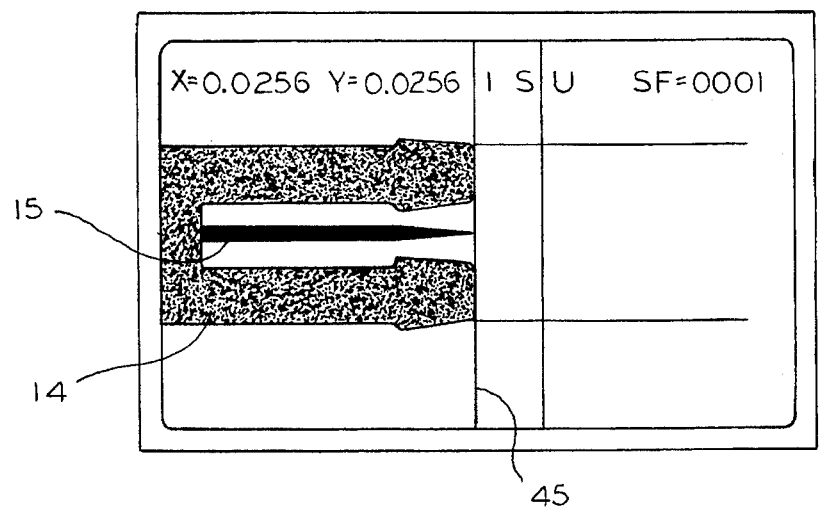
FIG. 6 is a view of the screen of the monitor of FIG. 3 showing the footplate of the knife of FIG. 1.
Figure 7:
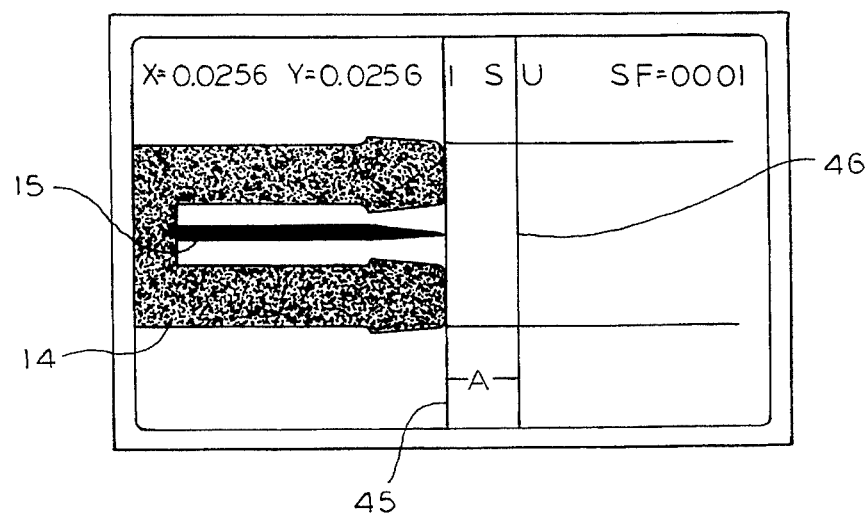
FIG. 7 is a view of the monitor of FIG. 5 showing the screen cursor offset.
Figure 8:
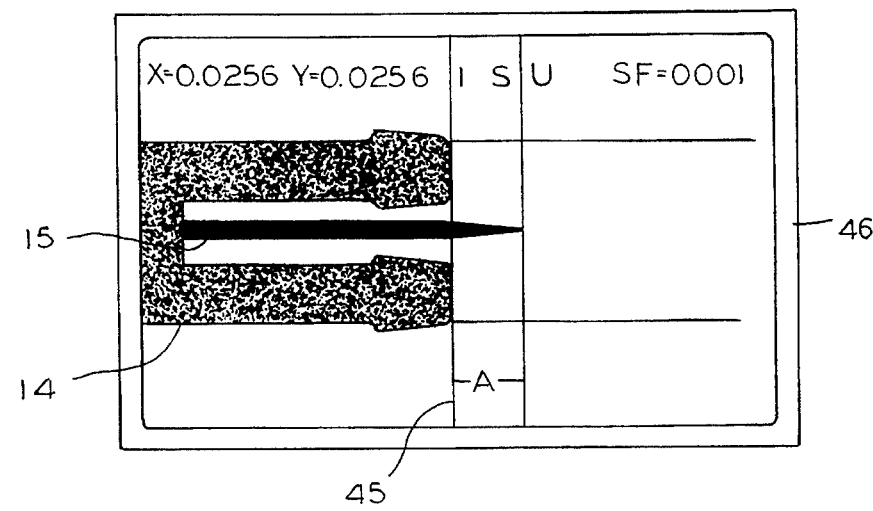
FIG. 8 is a view of the monitor of FIG. 5 showing the knife blade extended to the selected depth of cut.

Referring now to FIGS. 6–8, operation of the present invention may be fully described. As seen in FIG. 2, knife 10 is clamped to stage 23 of microscope 16. Stage 23 is then adjusted to bring footplate 14 of knife 10 into the field of view by using the x-axis and y-axis micrometer spindles 24 and 25, respectively. When properly positioned, footplate 14 appears as shown in FIG. 6.

Control console 28 is then used to create and position a reference or zeroing cursor 45, here shown in FIGS. 6, 7 and 8 as a straight line in the y-axis direction. Reference cursor 45 is then aligned with the edge of footplate 14 by using control console 28. Location of cursor 45 at the edge of footplate 14 is done by detecting variations in the signal generated by the video gun in monitor 27, finding the numeric midpoint of the slope of the signal variation and then using that data to calculate the on-screen position of reference cursor 45. Positioning of reference cursor 45 is accurate to one part in 1024.

Once reference cursor 45 has been positioned, micrometer mechanism 12 is used to advance blade 15 from knife 10 until blade 15 appears in the field of view and, as shown in FIG. 6, until the leading edge of blade 15 just reaches reference cursor 45. Blade 15 is then said to be in the "zeroed" position.

Referring now to FIG. 6, a set cursor 46, parallel to reference cursor 45, is generated by console 28, and is then moved electronically along the x-axis of monitor 27 by a selected distance equal to the cutting depth to which knife 10 is to be set. Prior to generating and positioning cursor 46, the image appearing on monitor 27 has been calibrated such that displacement of cursor 46 corresponds to an actual dimension with reference to footplate 14. As an example, if the cutting depth is to be 0.15 mm., the electronic, on-screen displacement A of cursor 46 from cursor 45 will, after calibration, correspond to an actual distance of 0.15 mm. with reference to knife 10.

Using micrometer mechanism 12, blade 15 is then advanced until, as shown in FIG. 8, the blade tip just reaches cursor 46. At that point, blade 15 has been advanced beyond footplate 14 by a distance A equal to the cutting depth.

The foregoing system can also be used to verify depth settings done previously or for knives with pre-set and non-adjustable settings by clamping the knife 10 into mounting block 26, moving the blade and footplate into the field of vision, aligning the reference cursor on the footplate and moving the set cursor to coincide with the blade tip while reading the on-screen dimension display.

The foregoing system can also be used to measure or set cutting depths for knives wherein the footplate is moved with reference to the blade, rather than vice versa.

By using the foregoing system, a surgeon can have an assistant manipulate the microscope and console controls to generate the required set cursor, leaving the surgeon to turn the micrometer mechanism to set the cutting depth. Such a method requires only that the knife itself and the mounting block be sterile, and does away with the need to sterilize or sheath any of the microscope controls that the surgeon would have to use if the microscope were used manually to visually set or verify cutting depth.

While the foregoing has described the present invention in terms of preferred embodiments thereof, such description is not intended to limit the scope of the invention. It is expected that others, skilled in the art, will perceive variations which, while differing from the foregoing, do not depart from the spirit and scope of the invention as herein described and claimed.

What is claimed is:

1. A method for setting a selected depth of cut of a surgical knife, said knife of the type having a handle, a datum surface attached to an end of said handle, a cutting blade and a mechanism for advancing said cutting blade to and beyond said datum surface, said depth of cut being determined by the distance a leading edge of said blade is positioned beyond said datum surface, said method comprising the steps of:

(a) securing said knife in a clamp mounted to a viewing stage of a microscope;

(b) moving said clamp to bring said datum surface into a field of view of said microscope;

(c) photographing said datum surface through said microscope with a video camera to generate a video signal;

(d) transmitting said video signal to a video monitor to produce a video image of said datum surface;

(e) calibrating said video image to correlate the on-screen dimensions of said video image with the actual dimensions of said knife;

(f) superimposing on said video image a reference cursor line;

(g) aligning said reference cursor line to coincide with said datum surface;

(h) generating on said monitor a second cursor line parallel to said reference cursor line;

(i) moving said second cursor line to a position apart from said reference cursor line by an on-screen distance correlated to the actual linear dimension of said selected depth of cut; and (j) advancing or retracting said blade until said leading blade edge reaches said second cursor line.

2. The method of claim 1 wherein step (a) includes the steps of:

(a1) mounting said clamp to a first platform moveable linearly with respect to said stage;

(a2) mounting said first platform to a second platform moveable linearly with respect to said stage in a direction at right angles to the direction of movement of said first platform; and (a3) mounting said second platform to said stage whereby moving said clamp is accomplished by moving said first and second platforms.

3. The method of claim 1 including interposing the following steps between steps (h) and (i):

(k) calculating continuously the correlated, on-screen distance between said reference and second cursors as said cursors are moved with respect to one another to determine the actual, linear distance represented by said on-screen distance; and (l) displaying continuously on said monitor said calculated distance as said cursors are moved with respect to one another.

4. The method of claim 3 including interposing the following steps between steps (j) and (k):

(k) calculating continuously the correlated, on-screen distance between said reference and second cursors as said cursors are moved with respect to one another to determine the actual, linear distance represented by said on-screen distance; and (l) displaying continuously on said monitor said calculated distance as said cursors are moved with respect to one another.

5. A method for verifying a depth of cut of a surgical knife, said knife of the type having a handle, a datum surface attached to an end of said handle and a cutting blade, said depth of cut being determined by the distance a leading edge of said blade is positioned beyond said datum surface, said method comprising the steps of:

(a) clamping said knife to the viewing stage of a microscope;

(b) moving said clamp to bring said datum surface and said leading edge into a field of view of said microscope;

(c) photographing said datum surface and said leading edge through said microscope with a video camera to generate a video signal;

(d) transmitting said video signal to a video monitor to produce a video image of said datum surface and said leading edge;

(e) calibrating said video image to correlate the on-screen dimensions of said video image with the actual dimensions of said knife;

(f) superimposing on said video image a reference cursor line;

(g) aligning said reference cursor line to coincide with said datum surface;

(h) generating on said monitor a second cursor line parallel to said reference cursor line;

(i) aligning said second cursor line to coincide with said leading edge;

(j) correlating the on-screen distance by which said reference and second cursor lines are separated to an actual linear dimension; and (k) comparing said dimension to said depth of cut.

6. The method of claim 5 wherein step (a) includes the steps of (a1) mounting said clamp to a first platform moveable linearly with respect to said stage;

(a2) mounting said first platform to a second platform moveable linearly with respect to said stage in a direction at right angles to the direction of movement of said first platform; and (a3) mounting said second platform to said stage whereby moving said clamp is accomplished by moving said first and second platforms.

7. Apparatus for setting or verifying the depth of cut of a surgical knife, said knife of the type having a handle, a datum surface attached to an end of said handle and a cutting blade, said depth of cut being determined by the distance a leading edge of said blade is positioned beyond said datum surface, said apparatus comprising:

a microscope having a viewing tube beneath which a viewing stage is positioned;

a platform assembly mounted to said viewing stage;

a clamp attached to said platform assembly, said clamp adapted to removably grip said surgical knife, said platform assembly having means for adjusting the position of said clamp and, thereby, said knife, to bring said datum surface into a field of view of said microscope;

means mounted on said viewing tube for broadcasting a video image of said field of view and, thereby, said datum surface; a video monitor;

means for transmitting said video image to said video monitor;

means for generating two or more cursor lines and superimposing said cursor lines on said video image;

means for changing the position of said cursor lines on said video image; and means for calibrating said video image to correlate movement of said cursor lines on said monitor with the actual, measured dimensions of said knife.

8. The apparatus as recited in claim 7 wherein said clamp is made from material which is sterilizable to a degree satisfactory for surgery.

* * * * *